United States Patent [19]

Venero et al.

[11] Patent Number: 5,011,928
[45] Date of Patent: Apr. 30, 1991

[54] ANALGESIC AND ANTIINFLAMMATORY DERIVATIVES OF 1-ACYL-4-ARYLALKYLPIPERAZINES

[75] Inventors: Aurelio O. Venero; Antonio T. Avello, both of Vizcaya, Spain

[73] Assignee: Fabrica Espanola de Productos Quimicos Y Farmeceuti Cos S.A. (FAES), Spain

[21] Appl. No.: 486,098

[22] Filed: Feb. 28, 1990

[30] Foreign Application Priority Data

Feb. 28, 1989 [EP] European Pat. Off. ........ 89500021.4

[51] Int. Cl.$^5$ .................. C07D 403/12; C07D 401/12; C07D 405/12; C07D 409/12
[52] U.S. Cl. ...................... 544/373; 544/230; 544/360; 544/367; 544/368; 544/372; 544/379; 544/386; 544/389; 544/390; 544/391
[58] Field of Search ............... 544/230, 360, 372, 373, 544/379, 386, 389, 390, 391, 367, 368

[56] References Cited

U.S. PATENT DOCUMENTS 4,656,175  4/1987  Björk et al. .................. 544/390
4,782,086 11/1988  Lunkenheimer et al. ......... 544/386

OTHER PUBLICATIONS

Valenta et al., Collection Czechoslovak Chem. Commun., vol. 52, 1987, pp. 3013-3023.
Yung et al., Chem. Abst., vol. 70, 47400r (1969).
Carron et al., Chem. Abst., vol. 76, 140165b (1972).
Ivanora et al., Chem. Abst., 87-33511s (1977).
Zikolova, Chem. Abst., 97-6257p (1982).
Witte et al., Chem. Abst., 99-105277t (1983).
Quittschorr et al., Chem. Abst., 104-186147x (1986).

*Primary Examiner*—Cecilia Shen
*Attorney, Agent, or Firm*—Wenderoth, Lind & Ponack

[57] ABSTRACT

The reaction of N-substituted piperazines with carboxylic acids or their active derivatives such as lower-alkyl esters or the acid chlorides, leads to the formation of new piperazine carboxamides of general structural formula I:

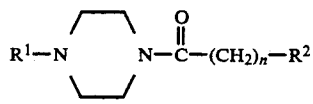

These compounds and the physiologically acceptable salts thereof are useful as analgesics and antiinflammatory agents.

5 Claims, No Drawings

ANALGESIC AND ANTIINFLAMMATORY DERIVATIVES OF 1-ACYL-4-ARYLALKYLPIPERAZINES

INTRODUCTION

The effective treatment of pain and inflammation remains one of the most important problems that therapeutic chemistry faces in the developped countries, due to the number of people affected and the social and economical consequences implied.

So. the work on non-opiate analgesic drugs is constantly increasing in medicinal chemistry aimed to the synthesis of more potent drugs, lack of central effects, as sedation, devoid of adverse reactions on the cardiovascular and respiratory systems, with long duration of action and a wide therapeutic index between analgesic and ulcerogenic doses. The previous work on analoesic and antiinflammatory compounds carried out in our laboratory as well as some precedent works reported in the literature (Zikolova et al., Farmatsiva (Sofia), 26(4), 10–14 (1976):Tr. Nauchnoizsled. Khim.-Farm. Inst. 11.12–19 (1981)) (Valenta et al., Collect. Czech. Chem. Commun. 52(12), 3013-23 (1987)) have lead us to investigate some new derivatives of piperazine carboxamides, the compounds of this invention, which are valuable as analgesic and antiinflammatory agents, represented by the general structural formula I:

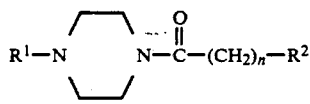

In which the substituent R1 may represent:
A lower-alkyl radical containing up to 4 carbon atoms such as methyl, ethyl, 1-methyl-ethyl or butyl.

An aryl-alkylene grouping AR—CH2—CH2, in which AR may have the following meanings:

phenyl or a phenyl radical substituted by from 1 to 2 of the following substituents: F, Cl, Br, I, CH3, C2H5, OH, OCH3, OCOCH3, CF3, NH2, NHCOCH3, NHSO2CH3, NO2 and COOH.

In which n=0, 1, 2.

In which the substituent R2 may represent the following radicals:
4-chlorophenyl, 3-chlorophenyl, 2-chlorophenyl, 4-methylphenyl, 3-methylphenyl, 2-methylphenyl, 4-hydroxyphenyl, 3-hydroxyphenyl, 2-hydroxyphenyl, 4-fluorophenyl, 3-fluorophenyl, 2-fluorophenyl, 4-acetoxyphenyl, 3-acetoxyphenyl, 2-acetoxyphenyl, 4-methoxyphenyl, 3-methoxyphenyl, 2-methoxyphenyl, 4-aminophenyl, 3-aminophenyl, 2-aminophenyl, 4-nitrophenyl, 3-nitrophenyl, 2-nitrophenyl, 2-thienyl, 3-thienyl, 2-furyl, 3-furyl, 2-pyridinyl, 3-pyridinyl, 4-pyridinyl, 2-thiazolyl, 3-methyl-2-thienyl, 5-methyl-2-thienyl, 5-methyl-3-methoxy-2-thienyl, 5-phenyl-3-methoxy-2-thienyl, 2-tetrahydrothienyl, 2-tetrahydrofuryl, 3-tetrahydrothienyl, 1H-2-isoindolyl-1,3(2H)-dioxo, 1-(1H-2-isoindolyl-1,3(2H)-dioxo)-ethyl, 1H-2-isoindolyl-1,3(2H)-dioxo-4,4a,5,6,7,7a-hexahydro, 1H-2-isoindolyl-1,3(2H)-dioxo-4,4a,7,7a-tetrahydro, 1H-2-isoindolyl-1,3(2H)-dioxo-4-nitro, 1H-2-isoindolyl-1,3(2H)-dioxo-4-amino, 1H-pyrrolyl-2,5-dihydro-2,5-dioxo, 1-pyrrolidinyl-2,5-dioxo, 8-azaspiro<4,5>decan-8-yl-7,9-dioxo, 1,2-benzoisothiazol-2-yl-6-carboxy-3(2H)oxo 1,1-dioxide, 1,2-benzoisothiazol-2-yl-3(2H)oxo 1,1-dioxide, 1,2-benzoisothiazol-2-yl-6-nitro-3(2H)oxo 1,1-dioxide, 1,2-benzoisothiazol-2-yl-6-amino-3(2H)oxo 1,1-dioxide, 1,2-benzoisothiazol-2-yl-6-acetylamino-3(2H)oxo 1,1-dioxide, 1,2-benzoisothiazol-2-yl-6-(methylsulfonylamino)-3(2H)oxo 1,1-dioxide, phenoxy, 4-methylphenoxy, 4-chlorophenoxy, 4-fluorophenoxy, 4-chloro-2-methylphenoxy, 4-acetoxyphenoxy, 3-acetoxyphenoxy, 4-hydroxyphenoxy, 3-hydroxyphenoxy, 4-aminophenoxy, 3-aminophenoxy, 4-nitrophenoxy, 3-nitrophenoxy, 3-methoxyphenoxy, amino, acetylamino, methylsulfonylamino, 2-(2-thienyl)-1-ethenyl, 2-(3-thienyl)-1-ethenyl, 2-(3-methyl-2-thienyl)-1-ethenyl, 2-(5-methyl-2-thienyl)-1-ethenyl, 2-(5-methyl-3-methoxy-2-thienyl)-1-ethenyl, 2-(5-phenyl-3-methoxy-2-thienyl)-1-ethenyl, 2-(5-chloro-2-thienyl)-1-ethenyl, 2-(3-chloro-2-thienyl)-1-ethenyl, 2-(3-hydroxy-2-thienyl)-1-ethenyl, 1-amino-ethyl, 1-acetylamino-ethyl and 1-(methylsulfonylamino)-ethyl.

The piperazines related to this invention are known products and may be represented by the general structural formula II:

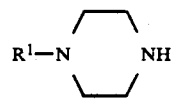

wherein R1 has the meanings formerly described.

The carboxylic acids which are reacted with the N-substituted piperazines to prepare the carboxamide compounds of the present invention, as well as their active derivatives such as lower-alkyl esters and acid chlorides are sufficiently known and many of them commercially available.

In some cases these products are not described in the literature, but may be easily prepared in good yields by well established procedures. For example, 2-tetrahydrothiopheneacetic acid is obtained from 2-tetrahydrothiophenecarboxylic acid (Wrobel et al., Synthesis 452 (1987)) through the Arndt-Eistert reaction.

In the production of the compounds of general structural formula I, as defined above, a carboxylic acid is reacted with a N-substituted piperazine to afford the corresponding carboxamide. It is advantageous to use an active derivative of the carboxylic acid such as the acid chloride or a lower-alkyl ester of the carboxylic acid, the process remaining essentially the same.

The compounds of the formula I are conveniently prepared as shown in the scheme (A):

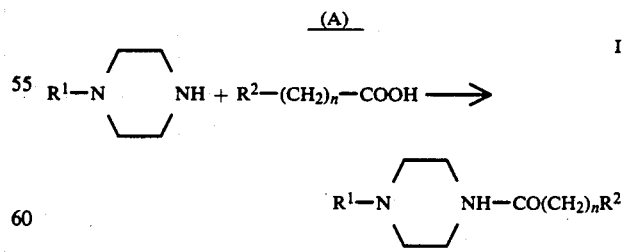

in which R1, n and R2 are described above. Thus, the appropriate substituted piperazine is reacted with the selected carboxylic acid in the presence of N,N'-dicyclohexyl-carbodiimide in an inert solvent such as dimethylformamide, tetrahydrofurane, dichloromethane or dioxane. The reaction is usually carried out at room temperature or below and is allowed to proceed for 6 to 48 h.

The compounds of the formula I may also be prepared as shown in scheme (B):

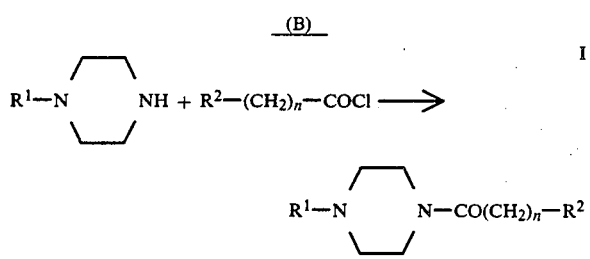

in which R1, n and R2 are described above. Thus, the appropriate substituted piperazine is reacted with the selected carboxylic acid chloride in an inert solvent such as diethyl ether, dioxane, tetrahydrofurane or dimethylformamide with or without a tertiary amine such as triethylamine. The reaction is carried out at temperatures from 0° C. to the reflux temperature of the solvent and is allowed to proceed for 2 to 24 h.

The compounds of the formula I may also be prepared as shown in scheme (C):

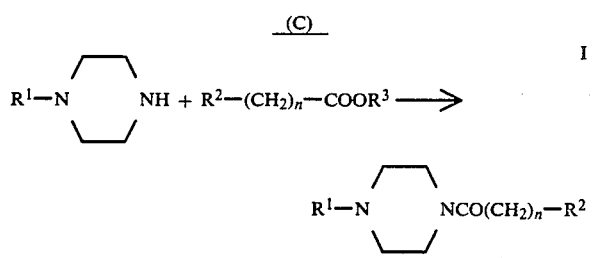

in which R1, n and R2 are described above. Thus, the appropriate substituted piperazine is reacted with the selected carboxylic acid lower-alkyl ester in an inert solvent of high boiling point, such as dimethylformamide, toluene or xylene, in the presence of 4A molecular sieves or p-toluenesulphonic acid. The reaction temperature is the boiling temperature of the reaction mixture and reaction is allowed to proceed for at least 12 h.

The following examples illustrate the preparation of compounds of formula I and as such are not to be considered as limiting the invention.

EXAMPLES

Example 1

1-<(4-Chlorophenyl)Acetyl>-4-(2-Phenylethyl)-Piperazine Hydrochloride

A solution of 0.01 mol of 4-chlorophenylacetyl chloride in 40 ml of dry tetrahydrofurane is dropwise added over a solution of 1.4 g (7.35 mmol) of 1-(2-phenylethyl)-piperazine in 50 ml of dry THF with strong stirring and keeping the reaction temperature below 20° C., by means of an external ice-water bath. After 2 h, the white solid is collected and washed thoroughly with tetrahydrofurane. Yield of the desired carboxamide hydrochloride: 90%.

(mp: 228°-231° C.) (C20H23ClN2O.HCl).

Example 2

1-<(4-Hydroxyphenyl)Acetyl>-4-(2-Phenylethyl)Piperazine

By the same method as that used in Example 1, starting from 4-acetoxyphenylacetic chloride, is prepared the hydrochloride of the corresponding carboxamide. The so obtained product, 0.01 mol, is dissolved in 100 ml of distilled water and 20 ml of 2N NaOH solution added and the whole mixture stirred for 8-10 h at 20° C. The pH of the resulting solution is adjusted to 8.5 by means of saturated NaHCO3 solution and the white crystalline solid filtered and washed with plenty of water. 8 mmol of the title compound are obtained (80%).

(mp: 150°-3° C.) (C20H24N2O2).

Example 3

4-(2-Phenylethyl)-1-<(2-Thienyl)Acetyl>-Piperazine Hydrochloride 0.01 Mol of 2-thiopheneacetic acid ethyl in 50 ml of dry xylene and 0.02 mol of 1-(2-phenylethyl)-piperazine are heated to reflux for 48 h in a continuous extraction Soxhlet-type system, the thimble of which contains 5 g of 4A molecular sieves. The reaction mixture is concentrated in vacuo to dryness and the residue crystallized from EtOH-H2O to afford the title compound as the free base. The hydrochloride salt is obtained by dissolving the base in 50 ml of absolute ethanol and saturating with dry HCl, whereupon the desired product crystallizes (Yield: 50%).

(mp: 179°-181° C.) (C18H22N2OS.HCl).

Example 4

4-(2-Phenylethyl)-1-<(3-Methoxy-5-Phenyl-2-Thienyl)Carbonyl>-Piperazine Hydrochloride Starting from 10 mmol of 5-phenyl-3-methoxy-2-thiophenecarboxylic acid chloride and 8 mmol of 1-(2-phenylethyl)-piperazine, and using a similar procedure to that described in Example 1, 2.65 g of the title compound are obtained (75%).

(mp: 227°-9° C.) (C24H26N2O2S.HCl).

Example 5

4-(2-Phenylethyl)-1-<1-Oxo-3-(2-Thienyl)-2-Propenyl>-Piperazine Hydrochloride

The title compound is obtained in 95% yield by a procedure similar to that described in Example 1, starting from 3-(2-thienyl)-2-propenoic acid chloride and 1-(2-phenylethyl)piperazine.

(mp: 230°-3° C.) (C19H22N2OS.HCl).

Example 6

4-(2-Phenylethyl)-1-<(2-Tetrahydro-Thienyl)-Carbonyl>-Piperazine Hydrochloride

The title compound is obtained in 80% yield by a procedure similar to that described in Example 1.

(mp: 206°-9° C.) (C17H24N2OS.HCl).

Example 7

1-<(2-Furyl)Carbonyl>-4-(2-Phenylethyl)-Piperazine Hydrochloride

The title compound is prepared from 2-furylcarboxylic acid chloride and 1-(2-phenylethyl)-piperazine in 95% yield, according to Example 1.

(mp: 183°-6° C.) (C17H20N2O2.HCl).

Example 8

1-<(1H-2-Isoindolyl-1,3(2H)-Dioxo)Acetyl>-4-(2-Phenylethyl)-Piperazine 0.01 Mol of 1,3(2H)-dioxo-1H-2-isoindoleacetic acid are dissolved in 50 ml of dry THF and 0.012 mol of DCC added while stirring and cooling, keeping the temperature of the reaction mixture below 15°-20° C. A heavy white precipitate is rapidly formed. Then, a solution of 8 mmol of 1-(2-phenylethyl)-piperazine in 50 ml of dry THF is introduced over 15-20 min, at such a rate to maintain the reaction temperature below 20° C. After stirring for 24 h, the mixture is filtered and the solution dried in vacuo. The residue is crystallized from EtOH-H2O to afford the title compound as a white crystalline solid (Yield: 70%).

(mp: 123°-6° C) (C22H23N3O3).

We claim:

1. Compounds of structural formula I:

$$R^1-N\overset{\frown}{\underset{\smile}{\phantom{XXX}}}N-\overset{O}{\underset{\|}{C}}-(CH_2)_n-R^2 \qquad I$$

wherein
the substituent $R^1$ is methyl, ethyl, 1-methyl-ethyl or 2-phenylethyl,
$n=0$, 1 or 2,
$R^2$ is selected from the group consisting of one of the following radicals:
4-chlorophenyl, 3-chlorophenyl, 2-chlorophenyl, 4-methylphenyl, 3-methylphenyl, 2-methylphenyl, 4-hydroxyphenyl, 3-hydroxyphenyl, 2-hydroxyphenyl, 4-fluorophenyl, 3-fluorophenyl, 2-fluorophenyl, 4-acetoxyphenyl, 3-acetoxyphenyl, 2-acetoxyphenyl, 4-methoxyphenyl, 3-methoxyphenyl, 2-methoxyphenyl, 4-aminophenyl, 3-aminophenyl, 2-aminophenyl, 4-nitrophenyl, 3-nitrophenyl, 2-nitrophenyl, 3-thienyl, 2-furyl, 3-furyl, 2-pyridinyl, 3-pyridinyl, 4-pyridinyl, 2-thiazolyl, 3-methyl-2-thienyl, 5-methyl-2-thienyl, 5-methyl-3-methoxy-2-thienyl, 5-phenyl-3-methoxy-2-thienyl, 2-tetrahydrothienyl, 2-tetrahydrofuryl, 3-tetrahydrothienyl, 1H-2-isoindolyl-1,3(2H)-dioxo, 1-(1H-2-isoindolyl-1,3(2H)-dioxo)-ethyl, 1H-2-isoindolyl-1,3(2H)-dioxo-4,4a,5,6,7,7a-hexahydro, 1H-2-isoindolyl-1,3(2H)-dioxo-4,4a,7,7a-tetrahydro, 1H-2-isoindolyl-1,3(2H)-dioxo-4-nitro, 1H-2-isoindolyl-1,3(2H)-dioxo-4-amino, 1H-pyrrolyl-2,5-dihydro-2,5-dioxo, 1-pyrrolidinyl-2,5-dioxo, 8-azaspiro<4,5>decan-8-yl-7,9-dioxo, 1,2-benzoisothiazol-2-yl-6-carboxy-3(2H)oxo 1,1-dioxide, 1,2-benzoisothiazol-2-yl-3(2H)oxo 1,1-dioxide, 1,2-benzoisothiazol-2-yl-6-nitro-3(2H)oxo 1,1-dioxide, 1,2-benzoisothiazol-2-yl-6-amino-3(2H)oxo 1,1-dioxide, 1,2-benzoisothiazol-2-yl-6-acetylamino-3(2H)oxo 1,1-dioxide, 1-2-benzoisothiazol-2-yl-6-(methylsulfonylamino)-3(2H)oxo 1,1-dioxide, phenoxy, 4-methylphenoxy, 4-chlorophenoxy, 4-fluorophenoxy, 4-chloro-2-methylphenoxy, 4-acetoxyphenoxy, 3-acetoxyphenoxy, 4-hydroxyphenoxy, 3-hydroxyphenoxy, 4-aminophenoxy, 3-aminophenoxy, 4-nitrophenoxy, 3-nitrophenoxy, 3-methoxyphenoxy, amino, acetylamino, methylsulfonylamino, 2-(2-thienyl)-1-ethenyl, 2-(3-thienyl)-1-ethenyl, 2-(3-methyl-2-thienyl)-1-ethenyl, 2-(5-methyl-2-thienyl)-1-ethenyl, 2-(5-methyl-3-methoxy-2-thienyl)-1-ethenyl, 2-(5-phenyl-3-methoxy-2-thienyl)-1-ethenyl, 2-(5-chloro-2-thienyl)-1-ethenyl, 2-(3-chloro-2-thienyl)-1-ethenyl, 2-(3-hydroxy-2-thienyl)-1-ethenyl, 1-amino-ethyl, 1-acetylamino-ethyl and 1-(methylsulfonylamino)-ethyl and the physiologically acceptable salts of such compounds.

2. Compounds of structural formula I:

$$R^1-N\overset{\frown}{\underset{\smile}{\phantom{XXX}}}N-\overset{O}{\underset{\|}{C}}-(CH_2)_n-R^2 \qquad I$$

wherein
the substituent $R^1$ is methyl, ethyl, 1-methyl-ethyl or 2-phenylethyl,
$n=0$,
$R^2$ is selected from the group consisting of one of the following radicals:
2-thienyl, 3-thienyl, 2-furyl, 3-furyl, 2-pyridinyl, 3-pyridinyl, 4-pyridinyl, 2-thiazolyl, 3-methyl-2-thienyl, 5-methyl-2-thienyl, 5-methyl-3-methoxy-2-thienyl, 5-phenyl-3-methoxy-2-thienyl, 2-tetrahydrothienyl, 2-tetrahydrofuryl, 2-(2-thienyl)-1-ethenyl, 2-(3-thienyl)-1-ethenyl, 2-(3-methyl-2-thienyl)-1-ethenyl, 2-(5-methyl-2-thienyl)-1-ethenyl, 2-(5-methyl-3-methoxy-2-thienyl)-1-ethenyl, 2-(5-phenyl-3-methoxy-2-thienyl)-1-ethenyl, 2-(5-chloro-2-thienyl)-1-ethenyl, 2-(3-chloro-2-thienyl)-1-ethenyl, 2-(3-hydroxy-2-thienyl)-1-ethenyl, 1-amino-ethyl, 1-acetylamino-ethyl, 1-(methylsulfonylamino)-ethyl and 1-(1H-2-isoindolyl-1,3(2H)-dioxo)-ethyl and the physiologically acceptable salts of such compounds.

3. Compounds of structural formula I:

$$R^1-N\overset{\frown}{\underset{\smile}{\phantom{XXX}}}N-\overset{O}{\underset{\|}{C}}-(CH_2)_n-R^2 \qquad I$$

wherein
$R^1$ is methyl, ethyl, 1-methyl-ethyl or 2-phenylethyl,
$n=1$,
$R^2$ represents a member selected from the group consisting of one of the following radicals:
4-chlorophenyl, 3-chlorophenyl, 2-chlorophenyl, 4-methylphenyl, 3-methylphenyl, 2-methylphenyl, 4-hydroxyphenyl, 3-hydroxyphenyl, 2-hydroxyphenyl, 4-fluorophenyl, 3-fluorophenyl, 2-fluorophenyl, 4-acetoxyphenyl, 3-acetoxyphenyl, 2-acetoxyphenyl, 4-methoxyphenyl, 3-methoxyphenyl, 2-methoxyphenyl, 4-aminophenyl, 3-aminophenyl, 2-aminophenyl, 4-nitrophenyl, 3-nitrophenyl, 2-nitrophenyl, 2-thienyl, 3-thienyl, 2-furyl, 3-furyl, 2-pyridinyl, 3-pyridinyl, 4-pyridinyl, 2-thiazolyl, 3-methyl-2-thienyl, 5-methyl-2-thienyl, 5-methyl-3-methoxy-2-thienyl, 5-phenyl-3-methoxy-2-thienyl, 2-tetrahydrothienyl, 2-tetrahydrofuryl, 1H-2-isoindolyl-1,3(2H)-dioxo, 1H-2-isoindolyl-1,3(2H)-dioxo-4,4a,5,6,7,7a-hexahydro, 1H-2-isoindolyl-1,3(2H)-dioxo-4,4a,7,7a-tetrahydro, 1H-2-isoindolyl-1,3(2H)-dioxo-4-nitro, 1H-2-isoindolyl-1,3(2H)-dioxo-4-amino, 1H-pyrrolyl-2,5- dihydro-2,5-dioxo, 1-pyrrolidinyl-2,5-dioxo, 8-azaspiro<4,5>decan-8-yl-7,9-dioxo, 1,2-benzoisothiazol-2-yl-6-carboxy-3(2H)oxo 1,1-dioxide, 1,2-benzoisothiazol-2-yl-3(2H)oxo 1,1-dioxide, 1,2-benzoisothiazol-2-yl-6-nitro-3(2H)oxo 1,1-dioxide, 1,2-benzoisothiazol-2-yl-6-amino-3(2H)oxo 1,1-dioxide, 1,2-benzoisothiazol-2-yl-6-acetylamino-3(2H)oxo 1,1-dioxide, 1,2-benzoisothiazol-2-yl-6-(methylsulfonylamino)-3(2H)oxo 1,1-dioxide, phenoxy, 4-methylphenoxy, 4-chlorophenoxy, 4-fluorophenoxy, 4-chloro-2-methylphenoxy, 4-acetoxyphenoxy, 3-acetoxyphenoxy, 4-hydroxyphenoxy, 3-hydroxyphenoxy, 4-aminophenoxy, 3-aminophenoxy, 4-nitrophenoxy, 3-nitrophenoxy, 3-methoxyphenoxy, amino, acetylamino and methylsulfonylamino and the physiologically acceptable salts of such compounds.

4. Compounds of structural formula I:

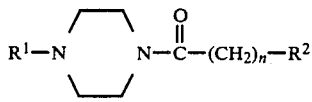

wherein
R$^1$ is methyl, ethyl, 1-methyl-ethyl or 2-phenylethyl,
n=2,
R$^2$ represents a member selected from the group consisting of the following radicals:
4-chlorophenyl, 3-chlorophenyl, 2-chlorophenyl, 4-methylphenyl, 3-methylphenyl, 2-methylphenyl, 4-hydroxyphenyl, 3-hydroxyphenyl, 2-hydroxyphenyl, 4-fluorophenyl, 3-fluorophenyl, 2-fluorophenyl, 4-acetoxyphenyl, 3-acetoxyphenyl, 2-acetoxyphenyl, 4-methoxyphenyl, 3-methoxyphenyl, 2-methoxyphenyl, 4-aminophenyl, 3-aminophenyl, 2-aminophenyl, 4-nitrophenyl, 3-nitrophenyl, 2-nitrophenyl, 2-thienyl, 3-thienyl, 2-furyl, 3-furyl, 2-pyridinyl, 3-pyridinyl, 4-pyridinyl, 2-thiazolyl, 3-methyl-2-thienyl, 5-methyl-2-thienyl, 5-methyl-3-methoxy-2-thienyl, 5-phenyl-3-methoxy-2-thienyl, 2-tetrahydrothienyl, 2-tetrahydrofuryl, 1H-2-isoindolyl-1,3(2H)-dioxo, 1H-2-isoindolyl-1,3(2H)-dioxo-4,4a,5,6,7,7a-hexahydro, 1H-2-isoindolyl-1,3(2H)-dioxo-4,4a,7,7a-tetrahydro, 1H-2-isoindolyl-1,3(2H)-dioxo-4-nitro, 1H-2-isoindolyl-1,3(2H)-dioxo-4-amino, 1H-pyrrolyl-2,5-dihydro-2,5-dioxo, 1-pyrrolidinyl-2,5-dioxo, 8-azaspiro<4,5>decan-8-yl-7,9-dioxo, 1,2-benzoisothiazol-2-yl-6-carboxy-3(2H)oxo 1,1-dioxide, 1,2-dioxide, 1,2-benzoisothiazol-2-yl-3(2H)oxo 1,1-dioxide, 1,2-benzoisothiazol-2-yl-6-nitro-3(2H)oxo 1,1-dioxide, 1,2-benzoisothiazol-2-yl-6amino-3(2H)oxo 1,1-dioxide, 1,2-benzoisothiazol-2-yl-6-acetylamino-3(2H)oxo 1,1-dioxide, 1,2-benzoisothiazol-2-yl-6(methylsulfonylamino)-3(2H)oxo 1,1-dioxide, phenoxy, 4-methylphenoxy, 4-chlorophenoxy, 4-fluorophenoxy, 4-chloro-2-methylphenoxy, 4-acetoxyphenoxy, 3-acetoxyphenoxy, 4-hydroxyphenoxy, 3-hydroxyphenoxy, 4-aminophenoxy, 3-aminophenoxy, 4-nitrophenoxy, 3-nitrophenoxy, 3-methoxyphenoxy, amino, acetylamino, methylsulfonylamino and the physiologically acceptable salts of such compounds.

5. The physiologically acceptable salts according to anyone of claims 1, 2, 3 or 4 wherein the physiologically acceptable salts are selected from the group consisting of the hydrochloride, hydrobromide, maleate, tartrate, citrate and ethanedioate of the compounds of formula I.

* * * * *